United States Patent [19]
McNaught et al.

[11] Patent Number: 5,977,454
[45] Date of Patent: Nov. 2, 1999

[54] HIGH AMYLOSE STARCH AND RESISTANT STARCH FRACTIONS

[75] Inventors: Kenneth J McNaught, North Epping; Eric Moloney; Ian L Brown, both of Tamworth; Adrian Timothy Knight, Lane Cove, all of Australia

[73] Assignee: Goodman Fielder Limited, New South Wales, Australia

[21] Appl. No.: 08/815,763

[22] Filed: Mar. 12, 1997

Related U.S. Application Data

[62] Division of application No. 08/374,645, filed as application No. PCT/AU93/00389, Jul. 30, 1993, Pat. No. 5,714,600.

[30] Foreign Application Priority Data

Jul. 31, 1992 [AU] Australia ................................. PL3894
Feb. 12, 1993 [AU] Australia ................................. PL7266

[51] Int. Cl.⁶ .............................. A01H 3/00; A01H 4/00; A01H 5/00; C12N 15/29
[52] U.S. Cl. ...................... 800/320.1; 800/295; 800/298; 800/263
[58] Field of Search .................................. 800/200, 230, 800/250, 205, DIG. 56, 295, 298, 263, 320.1; 47/58

[56] References Cited

U.S. PATENT DOCUMENTS

| | | | |
|---|---|---|---|
| 4,798,735 | 1/1989 | Friedman et al. | 426/578 |
| 5,004,864 | 4/1991 | Robertson et al. | 800/235 |
| 5,300,145 | 4/1994 | Fergason et al. | 106/213 |

FOREIGN PATENT DOCUMENTS

| | | |
|---|---|---|
| PL 0537 | 12/1992 | Australia. |
| 0 118 240 | 9/1984 | European Pat. Off.. |

OTHER PUBLICATIONS

Fractionation and Characterization of Dent Corn Amylomaize Starch Granules by J.E. Cluskey, C.A. Knutson and G.E. Inglett, Peoria—Starch/Starke 32(1980) Nr. 4.S. 105–109.

Ceral Chemistry;vol. 52, No. 6, Nov.–Dec., 1975.

Chemical Characteristics and Physico–chemical Properties of the Extruded Mixtures of Cereal Starches by L.Fornal et al, Starch/Starke 39 1987) Nr. 3, pp. 75–78.

Corn Harndess Determination, Y.Pomeranz et al; Cereal Chem 61(2):174–150, vol. 61, No. 2, 1984.

Vineyard and Bear. Corn Genet. Coop. Newsletter 26:5 (1952).

*Primary Examiner*—Lynette R. F. Smith
*Assistant Examiner*—Thomas Haas
*Attorney, Agent, or Firm*—McDermott, Will & Emery

[57] ABSTRACT

Hybrid maize seeds which yield a starch having an amylose content of 80% or more are disclosed as are starches having that amylose content. Compositions including these high amylose starches are also disclosed. Fractions of high amylose starches which have been formed on the basis of granule size are shown to have enhanced dietary fiber and/or resistant starch content. Such fractions enable the preparation of food compositions of enhanced dietary fiber and/or resistant starch content.

13 Claims, 4 Drawing Sheets

HIGH AMYLOSE STARCH AND RESISTANT STARCH FRACTIONS

This application is a division of application Ser. No. 08/374,645 filed Apr. 27, 1995, now U.S. Pat. No. 5,714,600 which is a filing under 35 USC 371 of PCT/AU93/00389, filed Jul. 30, 1993.

TECHNICAL FIELD

This invention relates to high amylose content starch, in particular to a maize starch having an amylose content of more than 80% w/w. The invention further relates to single, double and multiple cross maize hybrids, particularly to a maize single cross F1 hybrid, capable of producing grain having such a high amylose content and to this grain.

The invention still further relates to fractions of high amylose starch that are enriched in dietary fibre and resistant starch content whilst claiming a high amylose content.

BACKGROUND ART

Most common starches contain approximately 25% amylose and 75% amylopectin. Amylose is a linear glucose polymer fraction, whilst amylopectin is a branched glucose polymer fraction.

In the prior art, it has been recognized that currently available commercial starch having an elevated amylose content would impart certain desirable properties to various compositions including films, foods and industrial products. Accordingly, attempts have been made in the prior art to produce high amylose content maize. This is exemplified in AU-A-45616/89 wherein a maize seed deposited as ATCC No. 40499 is disclosed as capable of yielding a starch having an amylose content of up to 72%.

Typically, however, a commercial starch having an amylose content of 55–65% would be regarded in the art as having a high amylose content.

The present inventors whilst recognizing the utility of the commercially available so-called high amylose starches, have sought to produce a maize having a still higher amylose content.

DISCLOSURE OF INVENTION

In the course of a breeding program, a single cross F1 hybrid maize seed was produced, which carried the ae amylose extender gene. This seed was found to be capable of producing grain, in which the amylose content of the starch derived therefrom was in excess of 80%.

Accordingly, in a first aspect, this invention consists in a hybrid maize seed capable of producing a starch having an amylose content of more than 80%.

In a second aspect, this invention further consists in a maize starch having an amylose content of more than 80%, physically or chemically modified derivatives thereof, and destructurized and non-destructurized forms thereof.

In a third aspect, this invention still further consists in compositions including a maize starch selected from the group consisting of maize starch having an amylose content of more than 80%, physically or chemically modified derivatives thereof and destructurized and non-destructurized forms thereof.

In a fourth aspect, this invention still further consists in a process for the formation of a composition comprising including a maize starch selected from the group consisting of maize starch having an amylose content of more than 80%, physically or chemically modified derivatives thereof and destructurized and non-destructurized forms thereof, in said composition.

In a fifth aspect, the present invention still further consists in a hybrid maize seed resulting from a cross between any of the parental lines selected from the group consisting of G112, G113, G116, G117, G118, G119W, G120, G121, G122, G125W, G126, G128, G129, G135W, G136W, G138W, G139W, G140W and G144, said hybrid maize seed yielding a starch having an amylose content of more than 80%.

Starch granules from any botanical source are a heterogeneous mixture varying in physiological age and this affects their physical size, structure and properties. If the starch granules are physically separated according to their granule size, it has been noted by a number of authors that the properties of each size fraction are somewhat different. For example, Cluskey et al in Starke, 32, 105–109(1980) reported on the fractionation of dent corn and amylomaize starch granules. They found that an inverse relationship existed between granule size and iodine binding capacity in the amylomaizes. Thus, the percent apparent amylose found in the fractions of amylose V starch amounted to 40% for the largest size particles and 52% for the smallest particles.

The correlation between amylose content and size fraction has been observed by the present inventors in relation to high amylose starches of the type mentioned above and in co-pending patent application PL6537.

In this latter mentioned patent application, PL6537, it was disclosed that high amylose starches have a high dietary fibre or resistant starch content. More specifically, it was found that there was a correlation between amylose content and dietary fibre/resistant starch such that increasing levels of amylose above 55% were associated with increasing levels of dietary fibre/resistant starch.

Patent application PL6537 further disclosed the useful nature of such starches in the preparation of food compositions having an enhanced dietary or resistant starch content.

Based on the observations of
(1) an association of dietary fibre and resistant starch with increasing levels of amylose; and
(2) increasing amylose content with decreasing starch granule size,
it was to be expected that decreasing starch granule size fractions of high amylose starch would be associated with enhanced levels of dietary fibre and resistant starch.

Surprisingly, this was found to be incorrect. In fact it was found that there is an optimum starch granule size fraction which is intermediate in size and not necessarily associated with the highest amylose content fraction.

Accordingly in a sixth aspect, the present invention still further consists in a starch fraction of enhanced dietary fibre and/or resistant starch content comprising a high amylose starch which has been fractionated according to granule size to yield a fraction which is characterised by a dietary fibre and/or resistant starch content which is greater than said high amylose starch.

In a seventh aspect, the present invention still further consists in a food composition having an enhanced dietary fibre and/or resistant starch content, including a starch fraction of enhanced dietary fibre and/or resistant starch content derived from a high amylose starch which has been fractionated according to granule size to yield a fraction which is characterised by a dietary fibre and/or resistant starch content which is greater than said high amylose starch.

For the purpose of the description of this invention, "high amylose" means an amylose content (dsb) of 50% or more, preferably 70% or more, most preferably 80% or more. Particularly preferred amylose contents are 85% or more and 90% or more.

For the purposes of the description of the invention, the method by which amylose was determined is set out below.
Method: Apparent Amylose (Blue Value)
Scope: High Amylose Maize Starch
Apparatus:
Defatting
Soxhlet extraction apparatus
Steam bath
Whatman thimbles, 25×80 mm
Drying Oven 105° C.
Desiccator
Amylose Determination
Stoppered 50 ml test tubes
Vortex mixer
Boiling water bath
Spectrophotometer (605 mm, slit width 0.2 mm)
Reagents:
Defatting
Methanol (AR Grade)
Amylose Determination
Dimethylsulfoxide (HPLC Grade)
Iodine/Potassium iodide solution
  3.0 g iodine and 30 g potassium iodide made up to 1000 mls with 0.1 N sodium hydroxide
Methanol (AR Grade)
Amylose (Sigma Cat. No AO512)
  Dried for 2 hours at 105° C. prior to use.
Procedure:
Defatting
(1) Weigh 5 grams of starch into the thimble.
(2) Place the thimble in the Soxhlet apparatus.
(3) Extract the sample with methanol (200 mls) for 20 hours
(4) Recover the thimble and dry in an oven at 105° C. for 12 hours.
Amylose Determination
(1) Accurately weigh starch (100.0 to 105.0 mg) into the text tube.
(2) Add methanol (1 ml) and vortex mix.
(3) Add DMSO (15 mls), invert the test tube, and vortex mix.
(4) Place the test tubes in a vigorously boiling water bath for 60 minutes.
(5) Invert and vortex mix each test tube at 15 minute intervals during this period.
(6) Add distilled water (15 mls), invert and vortex mix. Place the test tube in the boiling water bath for a further 30 minutes.
(7) Quantitatively transfer the contents of the test tube to a 100 ml volumetric flask (use a funnel in the flask). Make the solution to volume with distilled water.
(8) Transfer an aliquot (3 mls) of this solution to a 100 ml volumetric flask and add 90 mls of distilled water.
(9) Add Iodine/Potassium Iodide solution (1 ml) to the diluted solution and immediately shake and mix thoroughly. Make to volume with distilled water.
(10) Measure the absorbance of this solution at 605 nm compared to a blank consisting of Iodine/Potassium Iodide solution (1 ml) diluted to 100 mls with distilled water in a volumetric flask.

Calculations:
For native starches:

$$\text{For native starches:} \quad \% \text{ Amylose } dsb = \frac{\text{Absorbance} \times 13}{\text{wt. sample } dsb}$$

*dsb=dry solids basis.

The method by which starch was separated from the maize grain was as follows:

1. Prepare 200 g meal by grinding through the 2 mm then the 1 mm screen of the Retsch Mill.
2. Wet thoroughly, stirring by hand, with 600 ml 0.1 N NaOH.
3. Add 2,200 ml 0.1 N NaOH and blend 5 minutes at ⅔ speed with the Ultra Turrax.
4. Sieve over 44 u screen.
5. Return sieve overs with 1L water and blend for another 3 minutes, if necessary.
6. Sieve over 44 u screen.
7. Centrifuge filtrate at 3000 rpm for 15 minutes. Decant. Wipe out the neck of the bottle with a tissue to remove fat.
8. Reslurry starch (centrifugate) with 200 ml water, i.e. 50 ml in each of 4 tubes. Centrifuge.
9. Remove starch from centrifuge tubes with about 250 ml water.
10. Adjust pH of starch slurry to 6.0–6.5 with 0.5 N HCl. Filter again over 44 u screen, if necessary.
11. Buchner filter and air dry.

MODES FOR CARRYING OUT THE INVENTION

In order to better understand the nature of this invention, a number of examples will be described.

Maize Seed

Figure 1:
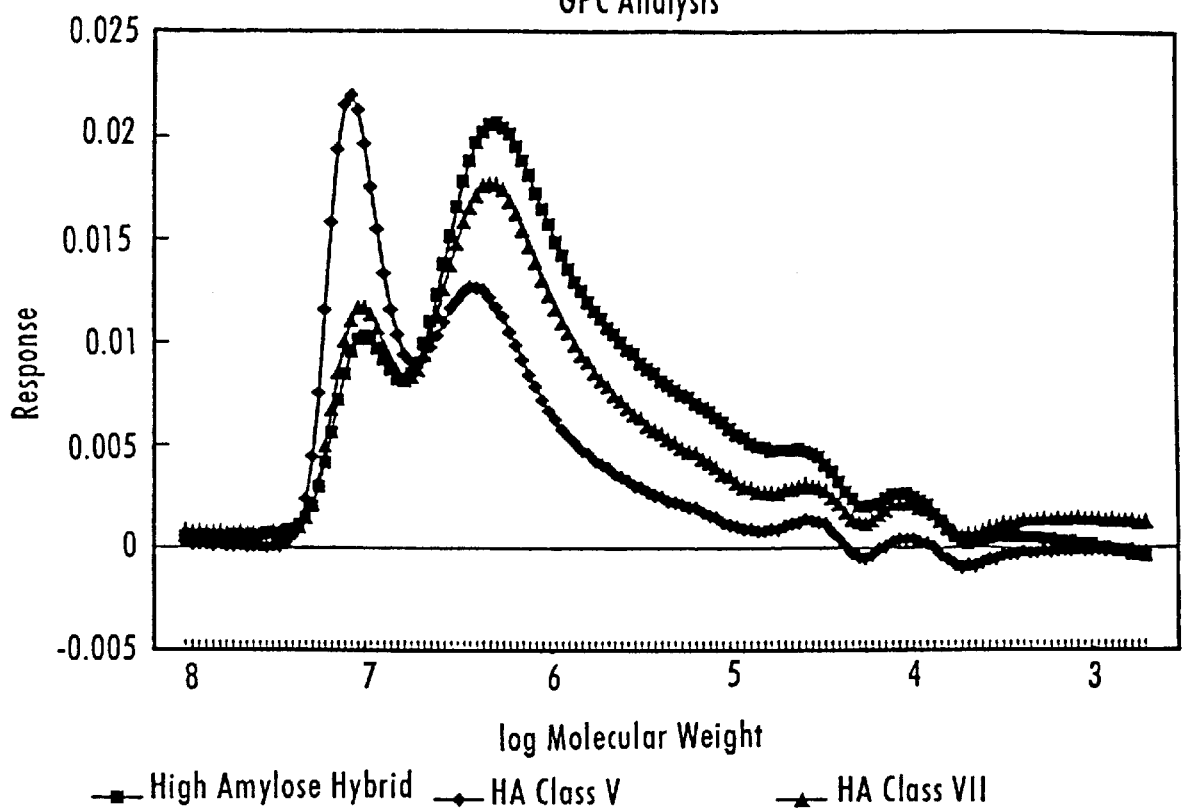
FIG. 1 is a gel permeation chromatography molecular weight profile of a number of maize starches.

A range of parental lines of maize seeds were obtained from High Yield Seed Co, Tamworth, Australia. Non-limiting examples of these parenting lines included G112, G113, G116, G117, G118, G119W, G120, G121, G122, G125W, G126, G128, G129, G135W, G136W, G138W, G139W, G140W and G144.

Hybrids were produced by crossing inbred lines carrying the ae amylose extender genes. These inbred lines were selected for combining ability and identified as specific female and male parents to produce the hybrids. Conventional breeding methods and techniques were used in developing inbred lines with repetitive amylose assays to ensure the transfer of recessively inherited ae gene.

One particular cross between male G116 and female G121 resulted in a F1 hybrid, referred to as Code 008 and deposited with the American Type Culture Collection (ATCC), 12301 Parklawn Drive, Rockville, Md.20853, U.S.A., under the designation 75182 on Jan. 15, 1992. This hybrid yielded grain the starch of which was found to have an amylose content in excess of 80%.

Based on the disclosure of this invention, the person skilled in the art would expect that hybrids resulting from further crosses of the parental lines mentioned above will yield starch having an amylose content in excess of 80%.

In fact experimental hybrids have yielded starches obtained from crosses between the above mentioned parent lines having high amylose contents. Set out below is a summary of the relevant crosses with amylose content in % bracketed.

|  | FEMALE | MALE | HYBRID |
|---|---|---|---|
| 1. | G117 (81.6) | G116 (82.2) | G117 × G116 (83.3) |
| 2. | G116 (82.2) | G122 (89.6) | G116 × G122 (80.5) |
| 3. | G118 (94.3) | G122 (89.6) | G118 × G122 (85.9) |
| 4. | G120 (94.6) | G122 (89.6) | G120 × G122 (80.4) |
| 5. | G122 (89.6) | G120 (94.6) | G122 × G120 (81.9) |
| 6. | G122 (89.6) | G140 (92.2) | G122 × G140 (85.4) |
| 7. | G128 (71.5) | G129 (61.8) | G128 × G129 (82.8) |
| 8. | G140 (93.2) | G121 (94.7) | G140 × G121 (93.0) |
| 9. | G140 (92.2) | G144 (60.4) | G140 × G144 (85.3) |
| * 10. | G139W (71.9) | G136W (93.4) | G139W × G136W (95.7) |
| 11. | G121 (94.7) | G126 (82.2) | G121 × G116 (85.0) |

* W = White seed.

Experiments conducted using Code 008 seed have shown that the climatic and agronomic conditions under which the maize is grown will have a significant effect on the amylose content. Specifically, it has been found that seed cultivated under irrigation near Tamworth, Australia (latitude 31.1° S) in an early crop and a late crop yielded starch having an amylose content respectively of 85.0% and 90.1%. Similarly, a crop cultivated at Finley, Australia (latitude 35.6° S) yielded starch having an amylose content of 94.8%. By contrast, the same seed when cultivated under irrigation at Giru, Australia (latitude 19.5°) yielded a starch having an amylose content of 78.6%.

Accordingly, a preferred embodiment of this invention comprises a maize seed deposited with the ATCC and designated 75182.

A further preferred embodiment of this invention comprises a maize starch having an amylose content of 85.0% or more, most preferably 90.1% or more.

To further characterize the maize starch derived from Code 008 grain, molecular weight profiling by gel permeation chromatography has been performed. The method by which this was done is set out below whilst the results are shown in the accompanying FIG. 1. For comparative purposes, two commercially available maize starches, HA Class V and HA Class VII are shown.

Method: Gel Permeation Chromatography of Starch
Scope: Starch
Apparatus:
  Sample Preparation
  Screw capped test tubes (50 ml)
  Boiling water bath
  Microcentrifuge (Eppendorf 5415)
  Desiccator
  HPLC
  Column Alltech GPC High MW Polar 5U (Cat. No. 100586)
  Detector Waters 410 Refractive Index Detector (X 128 35° C.)
  Pump Waters 600 E
  Injector Waters 712 WISP
  Column Heater (Set at 25° C.)
  Software Maxima 825 (V 3.3)
Reagents:
  Dimethyl sulfoxide (Chrom AR HPLC Grade—Mallinckrodt)
  Dimethyl formamide (Chrom AR HPLC Grade—Mallinckrodt)
  Pullulan Molecular Weight Standards—Showa Denko (ex Edward Instruments)
  HPLC Mobile Phase—DMSO:DMF (20:80)
Sample Preparation:
  Standards
  (1) The pullulan molecular weight standards need to be weighed into the screw capped test tubes in the following manner:
    Tube 1—5.0 mg each of P800, P100, P10 and glucose
    Tube 2—7.0 mg each of P400, P50 and P5
    Tube 3—7.0 mg each of P200, P20 and maltotriose.
  (2) Add DMSO (4 mls) to each tube and tightly seal it.
  (3) heat the tubes in the boiling water bath for 5 minutes to dissolve the pullulan.
  (4) Remove and cool the test tube to room temperature.
  (5) Add DMF (16 mls) and mix well.
  (6) Place 3×1.5 ml aliquots into microcentrifuge tubes and centrifuge at 14000 rpm for 10 minutes.
  (7) Remove the top 1 ml of solution from each centrifuge tube and place in a WISP vial.
  Samples
  (1) Accurately weight the sample (50.0 mg) into a screw capped test tube.
  (2) Add DMSO (10 mls).
  (3) Heat in a boiling water bath for 60 minutes.
  (4) Remove and cool the test tube to room temperature.
  (5) Add DMF (40 mls) and mix well.
  (6) Place 3×1.5 ml aliquots into microcentrifuge tubes and centrifuge at 14000 rpm for 10 minutes.
  (7) Remove the top 1 ml of solution from each centrifuge tube and place in a WISP vial.
HPLC Preparation
  (1) Prior to fitting the column, pump water (100 mls) through the HPLC.
  (2) Prepare the mobile phase and pump 50 mls through the HPLC. Ensure that the WISP is purged during this stage.
  (3) Adjust the flow rate of 0.2 ml/minute and connect the column.
  (4) Allow the column to equilibrate overnight.
  (5) Prior to the injection of samples, purge the WISP and then gradually increase the flow rate to 1.5 mls/minute.
  (6) Set the column heater to 25° C.
  (7) Inject the standards and samples—100 $\mu$l injection volume.
  (8) After samples have been analysed turn the column heater off and reduce the flow rate of 0.2 mls/minute.
  (9) Disconnect the column.
  (10) Wash the system with water overnight at 0.5 mls/minute.
  (11) Wash the system with methanol (200 mls).

Figure 2:
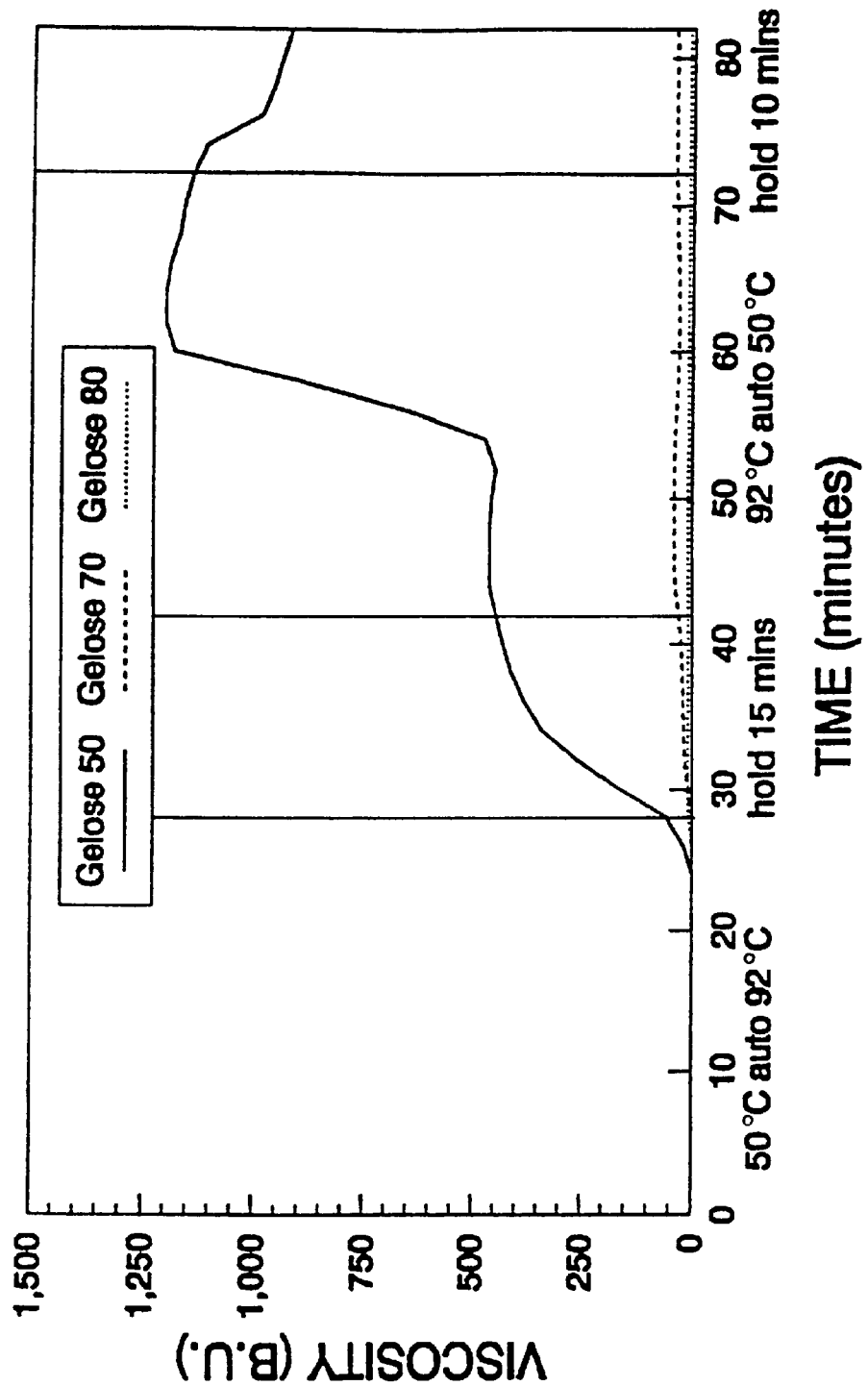
FIG. 2 is a viscograph of a number of maize starches in water.
Figure 3:
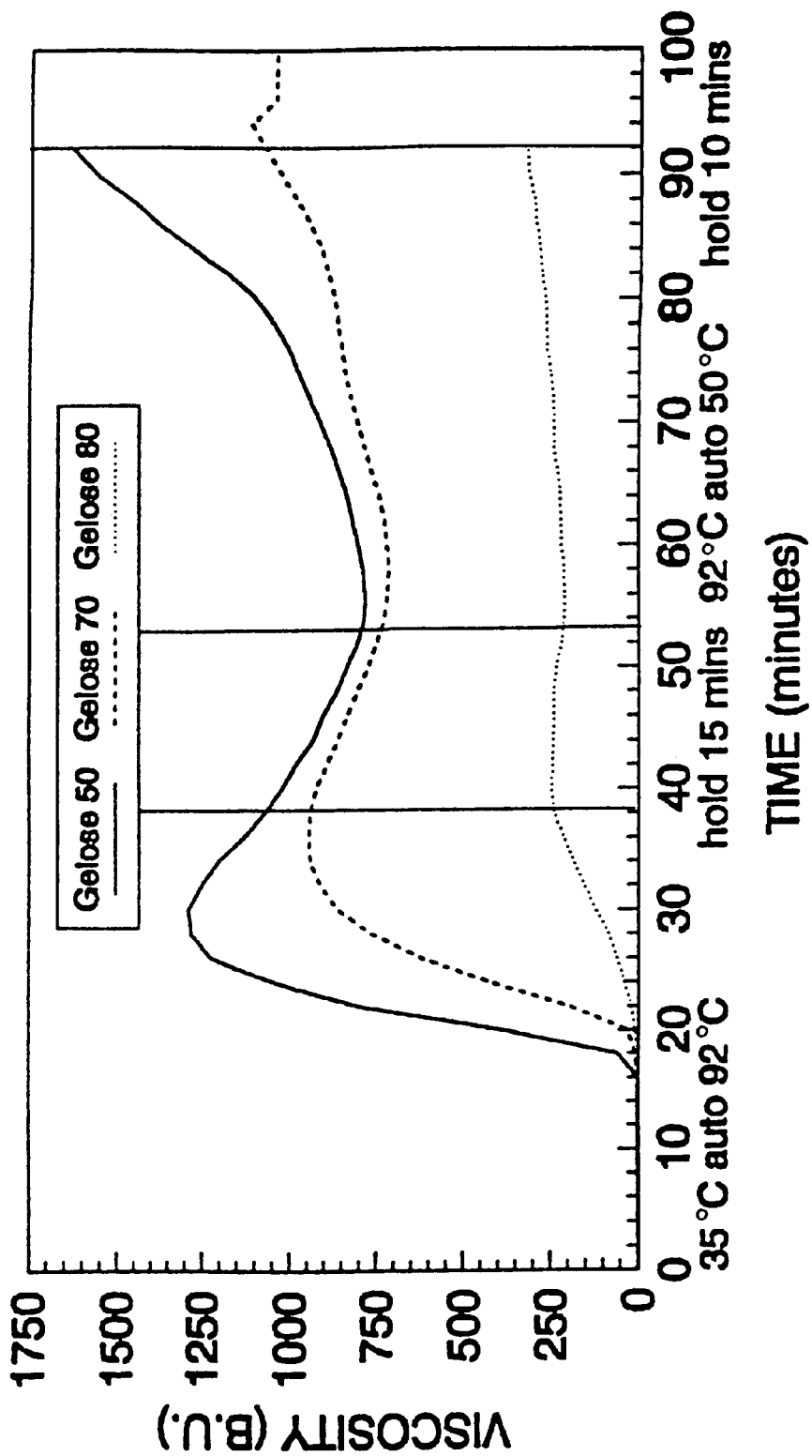
FIG. 3 is a viscograph of a number of maize starches in base.

Viscographs have also been prepared comparing maize starch from Code 008 (designated Gelose 80) with Gelose 50 and Gelose 70. FIG. 2 shows the viscosity profile under alkaline conditions whilst FIG. 3 shows the viscosity profile in water.

Maize Starch

The maize starch of the first aspect of this invention having an amylose content of more than 80% may be used in a variety of compositions known in the art. The usefulness of the starch is believed to be a result of the higher content of more linear molecules. This seems to impart physical properties which tend towards those of conventionally used synthetic plastics materials. Consequently, films formed from the starch of the invention have higher tensile strengths and are good oxygen barriers. The starch is also easier to process on existing synthetic plastics materials equipment such as blow moulding and injection moulding machines.

Furthermore, this starch may be physically modified or chemically modified to produce a variety of derivatives well known in the art. These starches may also be used in a variety of compositions.

Finally, this starch may also be used in processes and compositions requiring the starch to be destructurized within the meaning of that term defined in EP0118240.

Some non-limiting examples of compositions in which the maize starch of this invention in all of its forms, could be used include:
1. Corrugating adhesives.
2. Sausage skins.
3. Confectionery.
4. Other food compositions where the enhanced gel strength of the starch would be advantageous.
5. Films, either alone or laminated with polymers such as ethylenevinylalcohol to achieve both gas and water barrier properties.
6. Biodegradable and controlled release matrices and methods for forming and using these matrices as disclosed in PCT/AU90/00422, the contents of which is incorporated herein by way of reference.
7. Shaped articles, processes for forming shaped articles and methods for using shaped articles as disclosed in PCT/AU90/00237, the contents of which is incorporated herein by way of reference.
8. Coextrusions with synthetic polymers.
9. Intermediate products such as pellets and rods, formed for example by extrusion, and including combinations of starch with one or more natural or synthetic polymers, plasticizers, colourants and other additives.
10. Other blends of starch with natural or synthetic polymers to obtain enhanced structural properties.

Starch Fractions

The starches of the sixth and seventh aspects of this invention may originate from a number of sources including cereals such as maize, barley, wheat and legumes, providing that the starch content of such sources is high in amylose.

To fractionate the starch granules, there are a number of methods known in the art including dry powder sieving, hydrocyclone classification, air classification and differential sedimentation. A person skilled in the art would be readily able to choose an appropriate method depending on the source material and other relevant factors.

Although the size fraction of enhanced dietary fibre and/or resistant starch may vary, the example that follows describes the work that was done by the present inventors in relation to a maize starch sample. Based on this disclosure, a person skilled in the art could readily repeat this work using other starch sources to identify an appropriate fraction.

Once the starch has been appropriately fractionated, the fractions having enhanced dietary fibre and/or resistant starch content may be processed to obtain starch having further increased dietary fibre and/or resistant starch content using entirely conventional methods well known in the art. An example of the fractionation will now be described.

Fractionation of Maize Starch by Granule Size

A high amylose maize starch—High Amylose 80(10/91) was fractionated into seven subsamples based on granule size using the aqueous differential sedimentation procedure described by Cluskey et al (1980). This method was chosen since it minimised damage to the starch, did not introduce any residues and it was indicated that exposure of the starch granules to distilled water for long periods of time did not affect their integrity. Each subsample was weighed, measured for average granule size and the apparent amylose content, total dietary fibre and resistant starch determined. Each starch sample (60 grams) was separated into the seven fractions which were freeze-dried and weighed on a Mettler PE 3600 top pan balance. A scanning electron microscope was used to visually check the uniformity of the size distribution of the granules in each fraction.

Each fractionated starch sample was analysed for granule size according to the method described below. Apparent amylose content was determined using the method described above. Dietary fibre and resistant starch (McCleary et al) were determined using the methods disclosed in co-pending application PL6537.

Granule size was determined using a Malvern Master Sizer which utilises a He—Ne laser (632.8 nm) with a maximum output of 5 mW CW. In this method a starch slurry was made using approximately 15 mL of distilled water in a 50 mL beaker. The slurry was sonicated for 4 minutes. The slurry was then introduced into the stirred cell and the obscuration value adjusted using distilled water to 0.20. The slurry was allowed to stir for a further 2 minutes before readings were taken. Four readings were taken for each sample in order to check the stability of the readings being obtained.

RESULTS

Figure 4:
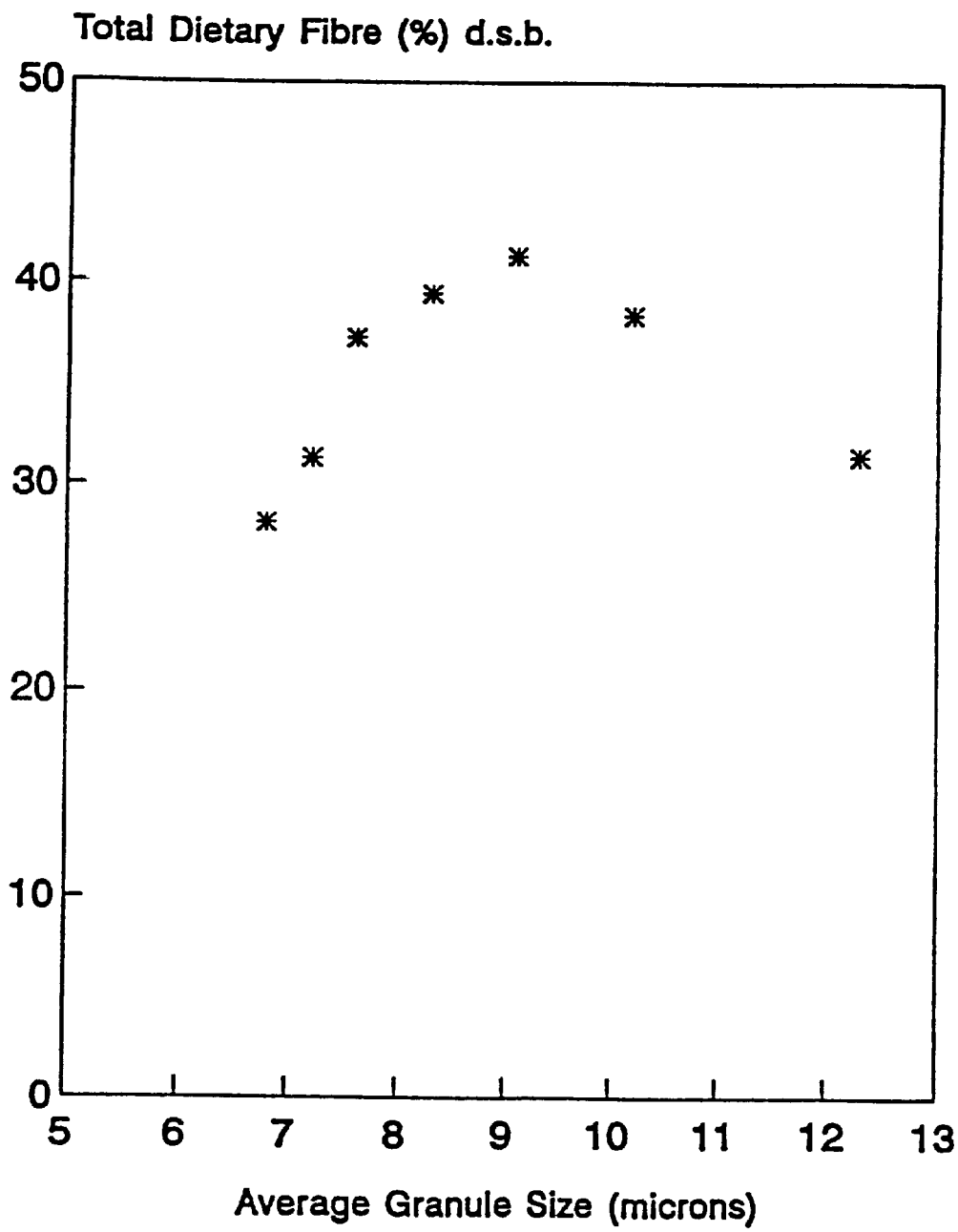
FIG. 4 is a graph of total dietary fibre versus average starch granule size.

In Table 1 set out below, there is shown the results (the average of two separate fractionations, together with the range of analytical results) obtained for each of seven particle size fractions. These results are graphically presented in FIG. 4, from which it is particularly evident that the level of resistant starch and dietary fibre is significantly increased between the second and fifth fractions, ie, 10.2–7.6 microns. Thus, if those starch fractions were to be segregated from the original starch sample, only 46.9% of the solids would need to be removed to produce a fraction in which the resistant starch was increased by 36% and dietary fibre by 24%.

Although the starch fractions of the invention are

TABLE 1

Fractionation of High Amylose 80 (10/91) Maize Starch by Granule Size

| | Amount in Fraction (%) dsb | Average Granule Size (microns) | Apparent Amylose Content (%) dsb | Total Dietary Fibre (%) dsb | Resistant Starch (%) dsb |
|---|---|---|---|---|---|
| High Amylose 80 - 10/91 | 100.00 | 10.0 | 85 | 33.4 | 18.1 |
| Fraction 1 | 35.6 ± 1.1 | 12.3 ± 0.5 | 80 ± 0 | 31.4 ± 1.5 | 17.7 |
| Fraction 2 | 15.0 ± 2.6 | 10.2 ± 0.1 | 83 ± 1 | 38.3 ± 2.0 | 16.4 |
| Fraction 3 | 13.0 ± 1.1 | 9.1 ± 0.2 | 85.5 ± 0.5 | 41.3 ± 0.3 | 22.8 |
| Fraction 4 | 14.9 ± 1.0 | 8.3 ± 0.1 | 85.5 ± 0.5 | 39.4 ± 4.1 | 24.6 |

TABLE 1-continued

Fractionation of High Amylose 80 (10/91) Maize Starch by Granule Size

| | Amount in Fraction (%) dsb | Average Granule Size (microns) | Apparent Amylose Content (%) dsb | Total Dietary Fibre (%) dsb | Resistant Starch (%) dsb |
|---|---|---|---|---|---|
| Fraction 5 | 10.2 ± 1.6 | 7.6 ± 0.1 | 88.5 ± 0.5 | 37.2 ± 1.3 | 18.9 |
| Fraction 6 | 7.0 ± 1.6 | 7.2 ± 0.1 | 89.5 ± 0.5 | 31.3 ± 2.4 | 21.7 |
| Fraction 7 | 4.3 ± 2.7 | 6.8 ± 0.2 | 89 | 28.1 | 10.1 | high in dietary fibre and/or resistant starch, it should also be appreciated that another important property is that these fractions are "naturally" derived. This arises out of the fact that the fractions are prepared using a physical means of separation. No chemical or other treatments are required in order to produce starch fractions having a high dietary fibre and/or resistant starch content. Such a property is of particular importance in food applications in that no regulatory approval would be required in order to incorporate such materials in food compositions.

The person skilled in the art will readily appreciate that the starch fractions of the invention having the enhanced dietary fibre and/or resistant starch content may be used in a variety of food compositions. Such uses are disclosed, for example, in co-pending application No PL6537.

Whilst it is not as yet known why the fractions of the invention have enhanced dietary fibre and/or resistant starch content, it will be appreciated by persons skilled in the art that numerous variations and/or modifications may be made to the invention as described without departing from the spirit or scope of the invention as broadly described. Accordingly, the Example based on a sample of high amylose maize starch is to be considered in all respects as illustrative and not restrictive.

The person skilled in the art will readily appreciate that the maize starch of the invention both in its native form, and the other forms mentioned above will have many applications additional to those mentioned.

It will also be appreciated by those skilled in the art that numerous variations and modifications may be made to this invention without departing from the spirit or scope thereof as broadly described.

We claim:

1. Hybrid maize seed carrying recessive ae amylose extender gene and containing starch having an amylose content of greater than 80% by weight.

2. The hybrid maize seed according to claim 1 containing starch having an amylose content of greater than 85% by weight.

3. The hybrid maize seed according to claim 1 containing starch having an amylose content of 90.1% weight.

4. The hybrid maize seed according to claim 1 containing starch having an amylose content of 94.8% weight.

5. Hybrid maize seed according to claim 1 produced by crossing inbred maize plants carrying the ae amylose extender gene.

6. The hybrid maize seed according to claim 1 produced from F1 maize plant hybrids.

7. The hybrid maize seed according to claim 1 which has all the characteristics of ATCC Accession No. 75182.

8. Hybrid maize seed carrying recessive ae amylose extender gene deposited under ATCC Accession No. 75182.

9. Maize plants grown from the hybrid maize seeds according to claim 8.

10. Viable maize seeds and plants and succeeding generations thereof grown from seeds deposited under ATCC Accession No. 75182, and maize seeds and plants carrying recessive ae amylose extender gene transferred from the deposited seeds and capable of producing starch having an amylose content of greater than 80% by weight.

11. Viable maize seeds and plants according to claim 10, capable of producing starch having an amylose content of greater than 85% by weight.

12. Viable maize seeds and plants according to claim 10 capable of producing starch having an amylose content of 90.1% by weight.

13. Viable maize seeds and plants according to claim 10 capable of producing starch having an amylose content of 94.8% by weight.

* * * * *